US009932446B2

(12) United States Patent
Nomura et al.

(10) Patent No.: US 9,932,446 B2
(45) Date of Patent: *Apr. 3, 2018

(54) METHOD OF MANUFACTURING A PURIFIED PRODUCT OF ALKYL-MODIFIED POLYDIMETHYLSILOXANE, A COSMETIC RAW MATERIAL, AND COSMETICS

(75) Inventors: Yasuo Nomura, Yokohama (JP); Keisuke Nishino, Hakusan (JP); Yasue Kanzaki, Chiba (JP)

(73) Assignee: DOW CORNING TORAY CO., LTD., Chiyoda-Ku, Tokyo (JP)

( * ) Notice: Subject to any disclaimer, the term of this patent is extended or adjusted under 35 U.S.C. 154(b) by 75 days.

This patent is subject to a terminal disclaimer.

(21) Appl. No.: 13/395,390

(22) PCT Filed: Sep. 8, 2010

(86) PCT No.: PCT/JP2010/065892

§ 371 (c)(1),
(2), (4) Date: Apr. 30, 2012

(87) PCT Pub. No.: WO2011/030914

PCT Pub. Date: Mar. 17, 2011

(65) Prior Publication Data

US 2012/0202893 A1    Aug. 9, 2012

(30) Foreign Application Priority Data

Sep. 10, 2009    (JP) ................. 2009-208768

(51) Int. Cl.
| A61K 8/58 | (2006.01) |
| C07F 7/08 | (2006.01) |
| C08G 77/34 | (2006.01) |
| A61K 8/06 | (2006.01) |
| A61K 8/891 | (2006.01) |
| A61Q 17/04 | (2006.01) |

(52) U.S. Cl.
CPC .............. *C08G 77/34* (2013.01); *A61K 8/064* (2013.01); *A61K 8/585* (2013.01); *A61K 8/891* (2013.01); *A61Q 17/04* (2013.01)

(58) Field of Classification Search
CPC ........ A61K 8/585; A61K 8/891; A61Q 17/04; C08G 77/34
USPC ................. 514/772; 556/456; 424/70.12
See application file for complete search history.

(56) References Cited

U.S. PATENT DOCUMENTS

| 6,784,271 B2 | 8/2004 | Nakanishi | |
| 2006/0135713 A1* | 6/2006 | Leclerc | C07D 271/06 526/204 |
| 2007/0166264 A1* | 7/2007 | Tamura et al. | 424/70.12 |
| 2010/0209367 A1* | 8/2010 | Lin | A61K 8/042 424/59 |

FOREIGN PATENT DOCUMENTS

| EP | 1734065 A1 | 12/2006 | |
| JP | H07-330907 A | 12/1995 | |
| JP | H09-165315 A | 6/1997 | |
| JP | H09-165318 A | 6/1997 | |
| JP | 11-335463 | * 12/1999 | ............. C08G 77/46 |
| JP | H11-335463 A | 12/1999 | |
| JP | 2000-327785 A | 11/2000 | |
| JP | 2003-012466 A | 1/2003 | |
| JP | 2003-048813 A | 2/2003 | |
| JP | 2003306550 A | 10/2003 | |
| JP | 2005-232235 A | 9/2005 | |
| WO | WO 02/055588 A1 | 7/2002 | |

OTHER PUBLICATIONS

English language abstract and machine-assisted English translation for JP H07-330907 extracted from the PAJ database dated Jan. 7, 2014, 27 pages.
English language abstract and machine-assisted English translation for JP H09-165315 extracted from the PAJ database dated Jan. 7, 2014, 44 pages.
English language abstract and machine-assisted English translation for JP H09-165318 extracted from the PAJ database dated Jan. 7, 2014, 41 pages.
English language abstract and machine-assisted English translation for JP H11-335463 extracted from the PAJ database dated Jan. 7, 2014, 32 pages.
English language abstract and machine-assisted English translation for JP 2000-327785 extracted from the PAJ database dated Jan. 7, 2014, 31 pages.
English language abstract for WO 02/055588 extracted from the espacenet.com database dated Jan. 7, 2014, 67 pages.
Nagasawa M. et al., Abstract of "Deoderization of Alkyl methyl Siloxane Wax for Cosmetic Raw Material, involves performing hydrogenation of Wax in Presence of Catalyst, Contacting Wax with Nitrogen Under Reduced Pressure and Distilling Light Material", WPI/ Thomson, vol. 2004, No. 20, Oct. 31, 2003, 2 pages.
English language abstract for JP2003306550 extracted from espacenet.com database dated Oct. 10, 2012, 6 pages.

(Continued)

Primary Examiner — Anna Falkowitz
(74) Attorney, Agent, or Firm — Howard & Howard Attorneys PLLC

(57) ABSTRACT

To provide a method for manufacturing a purified product of an alkyl-modified polydimethylsiloxane that is practically odorless and compatible with other cosmetic raw materials. The manufacturing method comprises the steps of: [A] synthesizing an alkyl-modified polydimethylsiloxane by subjecting a hydrosilyl-containing polydimethylsiloxane and an C2-C30 α-olefin to a hydrosilation reaction, and [B] subjecting the crude alkyl-modified polydimethylsiloxane obtained in Step [A] to a treatment of rendering it odorless by a hydrogenation reaction in the presence of a hydrogenation catalyst in an organic solvent (c) that is essentially free of active hydrogen atoms and has a boiling point equal to or greater than 70° C.

12 Claims, No Drawings

(56) References Cited

OTHER PUBLICATIONS

English language abstract and translation for JP 2003-012466 extracted from the PAJ database dated May 17, 2012, 67 pages.
English language abstract and translation for JP 2003-048813 extracted from the PAJ database dated May 17, 2012, 52 pages.
English language abstract for JP 2005-232235 extracted from the espacenet.com database dated May 17, 2012, 30 pages.
International Search Report for Application No. PCT/JP2010/065892 dated Jan. 19, 2011, 3 pages.

* cited by examiner ns and α-olefin in the presence of a platinum

METHOD OF MANUFACTURING A PURIFIED PRODUCT OF ALKYL-MODIFIED POLYDIMETHYLSILOXANE, A COSMETIC RAW MATERIAL, AND COSMETICS

RELATED APPLICATIONS

This application claims priority to and all the advantages of International Patent Application No. PCT/JP2010/065892, filed on Sep. 8, 2010, which claims priority to Japanese Patent Application No. JP2009-208768, filed on Sep. 10, 2009.

TECHNICAL FIELD

This invention relates to a method of manufacturing a purified product of an alkyl-modified polydimethylsiloxane and to cosmetics made therefrom, in particular, to a method of manufacturing a purified product of an alkyl-modified polydimethylsiloxane by subjecting a crude alkyl-modified polydimethylsiloxane to an odor-removing treatment by a hydrogenation reaction in an organic solvent that is essentially free from active hydrogen atoms. The invention also relates to a cosmetic raw material and to cosmetics that contain an odorless purified product obtained by the aforementioned method.

BACKGROUND ART

A polydimethylsiloxane modified with alkyl groups having 2 to 30 carbon atoms (hereinafter referred to as "an alkyl-modified polydimethylsiloxane") combines properties of both a silicone and an alkane and is characterized by excellent characteristics, such as lubricity, humectant (vapor obstructive) properties, adsorption residual properties, etc.

Alkyl-modified dimethylpolysiloxanes, especially those liquid polydimethylsiloxanes that are modified with alkyl groups that contain 4 to 18 carbon atoms, are superior in their handling properties to wax-type dimethylsiloxanes modified with long-chain alkyl groups, possess excellent emulsifiability and emulsion stability when used as oiling agents in emulsification systems of cosmetic products, and demonstrate pleasant coating sense and water repellency. Therefore, it is expected that such alkyl-modified dimethylsiloxanes will find wide application in the manufacture of shampoos, rinsing, hair-treatment, and sun-screen products, moisturization creams, or similar products (see, e.g., Patent References Nos. 1 to 3).

Generally, alkyl-modified polydimethylsiloxane is synthesized by a hydrosilation reaction (addition reaction) between polydimethylsiloxane having hydrosilyl groups (Si—H groups) and α-olefin in the presence of a platinum catalyst. However, an alkyl-modified polydimethylsiloxane synthesized by the above-described method is characterized by a specific (rather unpleasant) odor. One of the causes of this odor is α-olefin, which is used in an excessive amount during synthesis, remains as a residue in the reaction product (crude product), and generates an odor when oxidized. Patent Reference No. 3 discloses a method for producing a purified alkyl modified polydimethylsiloxane which is rendered substantially odorless by subjecting a crude product of an alkyl-modified polydimethylsiloxane to a hydrogenation reaction in an organic solvent such as an alcohol-type solvent, an ethyl-type solvent, or the like and in the presence of an hydrogenation catalyst. The aforementioned reference also discloses a cosmetic material that contains a purified product obtained by the above method.

However, a purified product of an alkyl-modified polydimethylsiloxane obtained by the above method overcomes the scent (unpleasant odor) odor only for a limited time and since such an odor significantly affects quality and applicability of cosmetic products, further improvement in odor-elimination properties is required.

[Patent Reference 1] JP 2003-012466 A
[Patent Reference 2] JP 2003-048813 A
[Patent Reference 3] JP 2005-232235 A

DISCLOSURE OF INVENTION

Technical Problems to be Solved

The present invention solves the problems of the prior art. It is an object of the invention to provide a method of manufacturing a purified product of a practically odorless alkyl-modified polydimethylsiloxane. It is another object to provide a cosmetic raw material and a purified product thereof that do not produce a specific odor due to the presence of an alkyl-modified polydimethylsiloxane. It is a further object to provide a cosmetic material that does not exude an unpleasant odor.

The inventors herein were confronted with a new technical problem, and the present invention is aimed exactly at a solution of this problem. More specifically, when a purified product of an alkyl-modified polydimethylsiloxane obtained by the method described in Patent Reference No. 3 is used, it does not demonstrate sufficient compatibility with other cosmetic raw materials, especially, with lipophilic components of cosmetic raw materials. In other words, when the purified product of the aforementioned alkyl-modified polydimethylsiloxane, in particular, a water-in-oil emulsion-type cosmetic raw material in which a purified product of the alkyl-modified polydimethylsiloxane is used as an oiling agent, this oiling agent demonstrates poor compatibility with other lipophilic components of the cosmetic raw material. Such incompatibility leads to white turbidity and loss of transparency of the cosmetic material, and makes such a raw material inapplicable to cosmetic products that need to have an attractive appearance.

In view of the above, in addition to the problems mentioned earlier, it is another object of the invention to provide a purified product of an alkyl-modified dimethylpolysiloxane that possesses excellent compatibility with other cosmetic raw materials and has excellent storage stability of obtained cosmetic product. Still another object is to provide a cosmetic raw material that contains the aforementioned purified product, and cosmetics comprising this raw material.

Solution to Problems

The above objects are achieved by a method of manufacturing a purified product of a polydimethylsiloxane modified with alkyl groups having 2 to 30 carbon atoms, the method comprising the step [A] of synthesizing a alkyl-modified polydimethylsiloxane by subjecting a hydrosilyl-containing polydimethylsiloxane and an α-olefin having 2 to 30 carbon atoms to a hydrosilation reaction, and the step [B] of subjecting the crude alkyl-modified polydimethylsiloxane obtained in Step [A] to a treatment of rendering it odorless by a hydrogenation reaction conducted at a temperature of 25° C. in the presence of a hydrogenation catalyst in an organic solvent (c) that is essentially free of active hydrogen atoms and has a boiling point that under a pressure of 1 atmosphere is equal to or greater than 70° C. Other objects of the invention are achieved by providing cosmetics that contain an alkyl-modified dimethylpolysiloxane obtained by the above-described method.

More specifically, the objects of the invention may be more preferably achieved by a method of manufacturing a purified product of a trisiloxane modified with alkyl groups having 2 to 30 carbon atoms, wherein a product of an alkyl-modified polydimethylsiloxane shown by general formula (3) given below is synthesized in a step [A1] by subjecting 1,1,1,3,5,5,5-heptamethyltrisiloxane and an α-olefin having 2 to 30 carbon atoms to a hydrosilation reaction, and then in a step [B1] subjecting the crude product of the alkyl-modified polydimethylsiloxane obtained in Step [A1] to a treatment of rendering it odorless by a hydrogenation reaction in an alkylcyclohexane (c1) having 7 to 9 carbon atom in the presence of a Raney nickel catalyst. Similarly, the object of the invention can be achieved by providing cosmetics that contain an alkyl-modified trisiloxane obtained by the above-described method.

In other words, the objects of the invention are achieved by the following manufacturing methods, cosmetic raw materials and cosmetics:

[1] A method of manufacturing a purified product of an alkyl-modified polydimethylsiloxane represented by the following general formula (1):

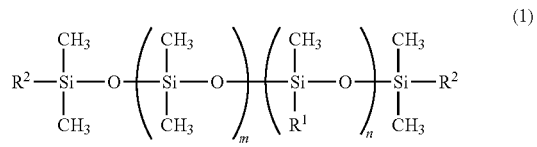

{where $R^1$ is an alkyl group of formula $-C_2H_4-C_pH_{2p+1}$ that contains 2 to 30 carbon atoms (where "p" is a number ranging from 0 to 28), and $R^2$ is a methyl group or a group defined earlier for $R^1$; "m" is a number ranging from 0 to 300; and "n" is a number ranging from 0 to 50; however, when "n" is 0, at least one $R^2$ is a group indicated by $R^1$}, the method comprising the following steps:

[A] synthesizing an alkyl-modified polydimethylsiloxane of general formula (1) by subjecting a hydrosilyl-containing polydimethylsiloxane (a) represented by the following formula (2):

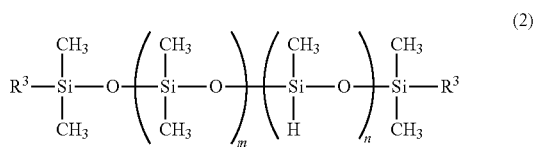

(where $R^3$ is a methyl group or a hydrogen atom; and "m" and "n" are number in the same ranges as defined earlier; however, when "n" is 0, at least one $R^3$ is a hydrogen atom) and an α-olefin of general formula $CH_2=CH-C_pH_{2p+1}$ (b) that contains 2 to 30 carbon atoms (where "p" is a number ranging from 0 to 28) to a hydrosilation reaction, and by [B] subjecting the crude alkyl-modified polydimethylsiloxane obtained in Step [A] to a treatment of rendering it odorless by a hydrogenation reaction that is carried out at a temperature of 25° C. in the presence of a hydrogenation catalyst in an organic solvent (c) that is essentially free of active hydrogen atoms and has a boiling point that is equal to or greater than 70° C. under a pressure of 1 atmosphere.

[2] The method of manufacturing a purified product of an alkyl-modified polydimethylsiloxane of [1], wherein the hydrogenation catalyst used in Step [B] is a Raney nickel, and the organic solvent (c1) is an alkylcyclohexane that contains 7 to 9 carbon atoms.

[3] The method of manufacturing a purified product of an alkyl-modified polydimethylsiloxane of [1] or [2], wherein step [A] comprises a step [A1] of synthesizing an alkyl-modified polydimethylsiloxane of formula (3) given below:

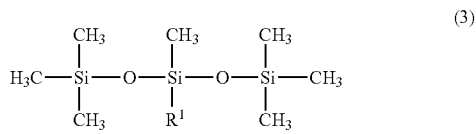

(where $R^1$ is the same as defined earlier) by subjecting 1,1,1,3,5,5,5-heptamethyltrisiloxane (a1) and an α-olefin of general formula $CH_2=CH-C_pH_{2p+1}$ that contains 2 to 30 carbon atoms (where "p" is a number ranging from 0 to 28) to a hydrosilation reaction, and wherein step [B] comprises a step [B1] of subjecting the crude alkyl-modified polydimethylsiloxane obtained in Step [A1] in the presence of a hydrogenation catalyst to a treatment of rendering it odorless by a hydrogenation reaction in an alkylcyclohexane (c1) that contains 7 to 9 carbon atoms.

[4] The method of manufacturing a purified product of an alkyl-modified polydimethylsiloxane according to any of [1] to [3], comprising a step of stripping of light fractions by distillation from the crude alkyl-modified polydimethylsiloxane or a product of hydrogenation thereof, prior or after Step [B], wherein the stripping is carried out by bringing the crude alkyl-modified polydimethylsiloxane or a product of hydrogenation thereof into contact with gaseous nitrogen under a reduced pressure.

[5] A cosmetic raw material that comprises a purified product of an alkyl-modified polydimethylsiloxane manufactured by a method according to any of [1] to [4].

[6] A cosmetic material that comprises a purified product of an alkyl-modified polydimethylsiloxane manufactured by a method according to any of [1] to [4].

[7] A cosmetic material that comprises a purified product of an alkyl-modified polydimethylsiloxane manufactured by a method according to any of [1] to [4] and one or more types of lipophilic cosmetic raw materials.

[8] A cosmetic material that comprises a purified product of an alkyl-modified polydimethylsiloxane manufactured by a method according to any of [1] to [4] and an organic UV absorber.

[9] A cosmetic material according to any of Items [6] to [8] that comprises a water-in-oil-type emulsion where an oiling agent is made from a purified product of an alkyl-modified polydimethylsiloxane manufactured by a method according to any of Items [1] to [4].

Advantageous Effects of Invention

The method of the invention provides a method of manufacturing a purified product of an alkyl-modified polydimethylsiloxane which is practically odorless. As an oil ingredient, the obtained alkyl-modified polydimethylsiloxane has excellent miscibility with components of cosmetic raw materials. The invention is also efficient in that it provides a cosmetic product and a cosmetic raw material that is free of a specific odor originated from the alkyl-modified polydimethylsiloxane and that comprise the aforementioned purified product of an alkyl-modified polydimethylsiloxane. The invention also provides cosmetics that comprise the aforementioned purified product of the alkyl-modified polydimethylsiloxane.

BEST MODE FOR CARRYING OUT THE INVENTION

The method of the invention for manufacturing a purified product of an alkyl-modified polydimethylsiloxane comprises the steps of:
[A] synthesizing an alkyl-modified polydimethylsiloxane of aforementioned general formula (I) by subjecting a hydrosilyl-containing polydimethylsiloxane (a) represented by the following formula (2):

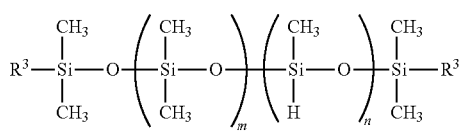

and an α-olefin (b) of general formula $CH_2=CH-C_pH_{2p+1}$ (where p is a number in the range of 0 to 28) that has 2 to 30 carbon atoms to a hydrosilation reaction;
[B] subjecting the crude alkyl-modified polydimethylsiloxane obtained in Step [A] to a treatment of rendering it odorless by a hydrogenation reaction that is carried out at a temperature of 25° C. in the presence of a hydrogenation catalyst in an organic solvent (c) that is essentially free of active hydrogen atoms and has a boiling point is equal to or greater than 70° C. under a pressure of 1 atmosphere.
<Step [A]>
Step [A] is synthesis of a crude alkyl-modified polydimethylsiloxane of general formula (1) by subjecting a hydrosilyl-containing polydimethylsiloxane represented by aforementioned formula (2) and an α-olefin that contains 2 to 30 carbon atoms to a hydrosilation reaction.

The aforementioned component (a) is a hydrosilyl-containing polydimethylsiloxane which, after a hydrosilation reaction with silicon-bonded hydrogen atoms having terminal carbon-carbon double bonds (Si—H) contained in the below-described component (b), forms an alkyl-modified polydimethylsiloxane. In the aforementioned formula, $R^3$ is a methyl group or a hydrogen atom, but when "n" is 0, at least one $R^3$ is a hydrogen atom. In other words, component (a) must contain in its molecule one or more silicon-bonded hydrogen atoms. In the formula, "m" is a number ranging from 0 to 300, preferably from 0 to 50, and most preferably from 0 to 6; "n" is a number ranging from 0 to 50, preferably from 1 to 20, and most preferably from 1 to 3.

It is most preferable for achieving the objects of the invention to have the value of "m" in general formula (2) equal to 0, and the value of "n" equal to 1. In that case, component (a) is represented by 1,1,1,3,5,5,5,-heptamethyltrisiloxane (a1).

Aforementioned component (b) is an α-olefin of general formula $CH_2=CH-C_pH_{2p+1}$ that contains 2 to 30 carbon atoms (where "p" is a number ranging from 0 to 28). In the alkyl-modified polydimethylsiloxane of the present invention, component (b) adds to the main molecular chain of the polydimethyl siloxane specific properties of an alkane. It is introduced to component (a) via the hydrosilation reaction.

Provided that the α-olefin has terminal carbon-carbon double bonds, it may have a linear, branched, or a partially cyclic molecular structure. However, when it is used as an oiling agent, then from the viewpoint of emulsifiability, emulsion stability, pleasant coating sense, water-repellancy, etc., it is recommended to use an α-olefin with the value of "p" in the range of 1 to 28, and preferably 2 to 28. It is also recommended to use a linear-chained α-olefin of general formula: $CH_2=CH-(CH_2)_q-CH_3$, wherein "q" is a number in the range of 1 to 27. A fluoroalkyl structure in which a part of hydrogen radicals is substituted with fluorine is also possible.

When the aforementioned α-olefin of component (b) is used in the production of a liquid middle chain alkyl modified polydimethylsiloxane purified product, it is recommended that the number of carbon atoms in the α-olefin is in the range of 4 to 18 (i.e., the value of "p" is in the range of 2 to 16), preferably 6 to 12 (the "p" value is in the range of 4 to 14), and further preferably 6 to 10 (the "p" number is in the range of 4 to 8). The most preferable α-olefin is 1-octane of formula $CH_2=CH-(CH_2)_5-CH_3$ with 8 carbon atoms. Such an α-olefin provides an alkyl-modified polydimethylsiloxane that, when used as an oiling agent, shows especially good properties of emulsifiability, emulsion stability, pleasant coating sense, water-repellency, etc.

The hydrosilation reaction for synthesizing the alkyl-modified polydimethylsiloxane can be performed by conventional methods with or without a solvent. Here, solvents suitable for the reaction may be represented by ethanol, isopropyl alcohol, or similar alcohols, by toluene, xylene, or similar aromatic hydrocarbons, by dioxane, THF, or similar ethers. It is required that, when the deodorization treatment of step [B] is performed after the hydrosilation reaction of step [A] by means of a hydrogenation reaction at 25° C. without solvent exchange, such a treatment be carries out in an organic solvent that under a pressure of 1 atmosphere has a boiling point of 70° C. or higher and is practically free of active hydrogen atoms.

The hydrosilation reaction can be carried out with or without the presence of a catalyst, but the presence of a catalyst is preferable for shortening the reaction time and for the possibility of conducting the reaction at low temperatures. Catalysts suitable for the reaction are exemplified by platinum, ruthenium, rhodium, palladium, osmium, iridium, or similar compounds. Most preferable of these are platinum-type compounds since they possess a high catalytic activity. Examples of platinum-type catalysts are the following: chloroplatinic acid; metal platinum; metal platinum on a carrier such as alumina, silica, carbon black, etc.; platinum-vinyl siloxane complexes, platinum-phosphine complexes, platinum-phosphite complexes, and platinum alcoholate catalysts, or similar complexes. When platinum-type catalysts are used, they should contain metal platinum in an amount of 0.5 to 100 ppm.

Usually the hydrosilation reaction should be carried out at a temperature of 50 to 150° C., and the reaction time is usually in the range of 10 minutes to 24 hours, preferably 1 to 10 hours. The hydrosilation reaction synthesizes an alkyl-modified polydimethylsiloxane of formula (1) given below and thus produces a crude product.

General formula (1):

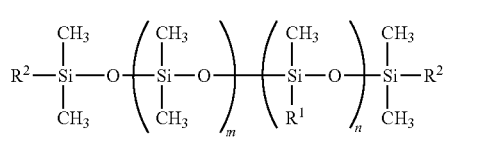

In the above formula, $R^1$ is an alkyl group of formula $-C_2H_4-C_pH_{2p+1}$ that contains 2 to 30 carbon atoms (where "p" is a number ranging from 0 to 28), i.e., a group that originates from α-olefin having 2 to 30 carbon atoms; the preferable values of "p" being in the same range as mentioned earlier; $R^2$ is a methyl group or a group defined earlier for $R^1$; and "m" and "n" are the same as defined earlier in connection with formula (2). However, when "n" is 0, at least one $R^2$ is a group indicated by $R^1$.

An example of alkyl-modified polydimethylsiloxane most suitable for use as a cosmetic raw material is an alkyl-modified polydimethylsiloxane of general formula (3) given below with a main chain formed by a trisiloxane. The alkyl-modified polydimethylsiloxane represented by general formula (3) is synthesized by subjecting a 1,1,1,3,5,5,5-hepthamethyltrisiloxane (which is an appropriate hydrosilyl-containing polydimethylsiloxane) and an α-olefin to a hydrosilation reaction.

General formula (3):

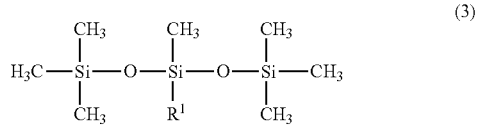

(where $R^1$ is represented by the same groups as those defined earlier).

Specific examples of the alkyl-modified polydimethylsiloxane represented by the aforementioned general formula (3) can be exemplified by compounds which are expressed by formulae (I) through (VII).

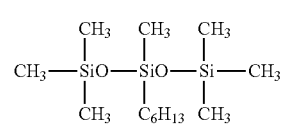

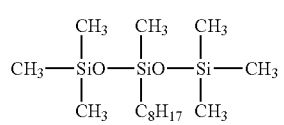

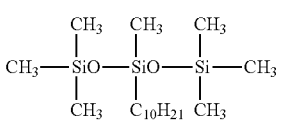

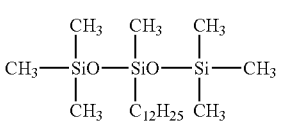

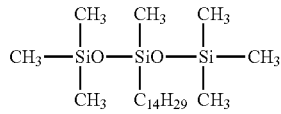

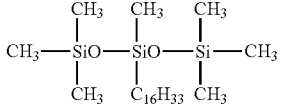

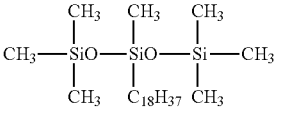

An internal rearrangement of double bonds in the α-olefin may occur in the hydrosilation process as a side reaction that may produce by-products that do not participate in a reaction of addition to hydrosilyl groups.

On the other hand, the target product becomes unstable if it contains highly reactive hydrosilyl groups. Therefore, generally the charges of α-olefins and hydrosilyl-containing polydimethylsiloxane of component (a) and α-olefin of component (b) are adjusted (by supplying an accessed amount of α-olefin) so as to obtain an excess of unsaturated groups as compared to hydrosilyl groups. For this reason, the crude product of the alkyl-modified polydimethylsiloxane obtained as a result of the hydrosilation reaction will inevitably contain unreacted α-olefins and internally rearranged olefins.

However, by selecting an α-olefin for use in the method of the present invention with a number of carbon atoms in the range of 4 to 18 (and hence, with a relatively low boiling point), it becomes possible to relatively easily remove the aforementioned unreacted α-olefins. Furthermore, by selecting component (a) with "m" in the range of 0 to 6 and with "n" in the range of 1 to 3, it is possible to provide component (a) with a relatively low molecular weight, and hence, with high volatility. Therefore, by adding the component in an excessive amount upon completion of the hydrosilation reaction, it will be possible to remove the unreacted hydrosilyl-containing polydimethylsiloxane and the light components that contain the internally rearranged olefins. The process of removal of light substances that contain the unreacted α-olefin and the hydrosilyl-containing polydimethylsiloxane, as well as the internally rearranged polyolefin (i.e., the Step of stripping) is described below.

<Step [B]>

Step [B] is a process of deodorization by subjecting the crude product of the alkyl-modified polydimethylsiloxane obtained in step [A] to hydrogenation at 25° C. in the presence of a hydrogenation catalyst and in an organic solvent (c) that is essentially free of active hydrogen atoms and has a boiling point that under a pressure of 1 atmosphere is equal to or greater than 70° C.

Deodorization treatment by means of the hydrogenation reaction is performed in the presence of a hydrogenation catalyst. Hydrogenation catalysts suitable for the aforementioned reaction may be catalysts of precious metal type such as platinum or palladium catalysts, or catalysts of a nickel system. Specific examples of such catalysts are the following: nickel, palladium, platinum, rhodium, or similar elements used individually, or catalysts compounded from several metals such as platinum-palladium, nickel-copperchromium, nickel-copper-zinc, nickel-tungsten, nickel-molybdenum, etc. The catalysts may be supported by arbitrary carriers such as activated carbon, silica, silica alumina, alumina, zeolite, etc. The carried amount of metal may, for the catalysts of precious metals, be in the range of 0.1 to 5 mass %, preferably 0.2 to 3 mass %, and for the catalysts of the nickel system in the range of 20 to 70 mass %, and preferably 40 to 60 mass %. Moreover, the platinum catalyst used in the synthetic process (hydrosilation reaction) can also be used as it is. The hydrogenation catalysts can be used individually or in combinations of two or more.

The hydrogenation catalyst most suitable for Step [B] is a nickel-type catalyst, a "nickel/diatomaceous earth" type catalyst, or a Raney catalyst. For enhancing the deodorization by hydrogenation, the Raney catalyst is preferable.

A distinguishing feature of the invention is that the hydrogenation reaction that is conducted, in particular, in Step [B], is carried out at a temperature of 25° C. in an organic solvent (c) that is essentially free of active hydrogen atoms and has a boiling point that under a pressure of 1 atmosphere is equal to or greater than 70° C. In the context of the present invention the term "active hydrogen atoms" means hydrogen atoms which have reactivity with respect to residual hydrosilyl groups of aforementioned component (a). More specifically, what is meant is hydrogen atoms bonded to oxygen-containing hydroxyl groups (—OH) or carboxyl groups (—COOH). An advantage of component (c) of the present invention is that such an organic solvent is practically free of active hydrogen atoms, has a limited reactivity with respect to residual hydrosilyl groups of component (a), and is characterized by good compatibility with the alkyl-modified polydimethylsiloxane obtained after purification, as well as with other cosmetic material components.

Another advantage of the organic solvent of component (c) is that it has a boiling point that under a pressure of 1 atmosphere is equal to or greater than 70° C. and that during the hydrogenation reaction that is carried out at a temperature of 25° C., especially with the use of a Raney catalyst, it is possible to suppress ignition. On the other hand, the organic solvent of component (c) can be easily removed in the process of stripping light substances when the product is brought in contact with nitrogen gas. Therefore, it is preferable that the boiling point of the organic solvent is in the range of 70° C. to 230° C., and more preferably in the range of 70° C. to 100° C.

Specific examples of component (c) are the following organic solvents used individually or in combinations: 1-heptane, or similar alkanes having 7 to 12 carbon atoms; cyclohexane, or similar cycloalkanes having 6 to 10 carbon atoms; methylethylketone, methylisobutylketone, cyclohexanone, or similar ketones having 4 to 10 carbon atoms; ethylacetate, or similar esters. An advantage of using such organic solvents is that the obtained crude products of the alkyl-modified dimethylpolysiloxane obtained as a result of the hydrogenation reaction are practically free of any odor, and the ether-like scent is almost completely imperceptible.

Cycloalkanes having 6 to 10 carbon atoms, especially alkylcyclohexane-type solvents having 7 to 9 carbon atoms are most suitable for use as component (c). In particular, when the hydrogenation reaction is carried out in an alkoxycyclohexane-type solvent that comprises one or several solvents selected from the group consisting of methylcyclohexane, ethylcyclohexane, dimethylcylcohexane, trimethylcyclohexane, ethylmethylcyclohexane, and propylcyclohexane, it becomes possible to easily obtain large quantities of purified products of alkyl-modified polydimethylsiloxane that is practically odorless. When such products are used as oil ingredient, they demonstrate excellent compatibility with other cosmetic raw materials.

The hydrogenation reaction can be performed under normal pressure or under increased pressure. In fact, the reaction is carried out in pressurized hydrogen (hydrogen pressure is in the range of 0.1 to 20 MPa, i.e., 1 to 200 kg/cm$^2$). The reaction is carried out at a temperature of 0 to 200° C. A temperature of 50° C. to 170° C. is most suitable for shortening the reaction time.

The hydrogenation reaction can be carried out as a batch process or as a continuous process. In a batch process, the reaction time depends on factors such as the amount of the catalyst, reaction temperatures, etc., but, in general, the reaction continues for 1 to 10 hours. In a batch process, the terminal point of a hydrogenation reaction can be considered to be the time during which the decrease in pressure of hydrogen is no longer observed after the reaction is continued for an additional 1 to 2 hours. If hydrogen pressure decreases in the course of the reaction, it is recommended to repeat the introduction of hydrogen and to maintain it under increased pressure in order to shorten the reaction time.

After completion of the hydrogenation reaction, the hydrogenation reaction catalyst (which is a hydrosilation catalyst if it is present in the reaction system) is separated in a pressurized nitrogenous atmosphere by using filter paper, diatomaceous earth, or activated carbon.

<Stripping Process>

In the method of the invention, prior to and/or after step [B], it is desirable to subject a crude product of the alkyl-modified polydimethylsiloxane and/or a product of hydrogenation, to stripping of light substances by bringing the product in contact with gaseous nitrogen and distilling the light substances under reduced pressure.

In the context of the present invention, in addition to reaction solvents used in the hydrosilation reaction (i.e., in step [A] and/or in hydrogenation reaction (step [B]), the term "light substances", which are distilled by the stripping process, also covers the unreacted α-olefin or hydrosilyl-containing polydimethylsiloxane that is used in an excessive amount and remains in the reaction product after step [A], as well as the internally rearranged olefins and olefin hydrates that constitute by-products.

A stripping process (distillation of light substances) may be carried out prior to step [B] by treating the crude product of the alkyl-modified polydimethylsiloxane, or after completion of step [B] by treating the product of hydrogenation of the alkyl-modified polydimethylsiloxane. If necessary, the stripping process can be carried out in both cases, i.e., prior to and after step [B].

According to one example of distillation of light substances, the crude product or product of hydrogenation which contains a light substance is loaded into a flask equipped with a reflux cooling pipe, nitrogen supply pipe, etc. During supply of nitrogen to the flask, pressure is reduced, and temperature is increased. During distillation of light substances, however, pressure and temperature are kept constant. In the method of the invention, the reduced pressure conditions is in the range of 0.1 to 10.0 KPa, heating conditions is in the range of 50° C. to 170° C., and treatment time may be in the range of 10 min. to 24 hours.

<Purified Product of Alkyl-Modified Polydimethylsiloxane>

A purified product of the alkyl-modified polydimethylsiloxane represented by aforementioned general formula (1) is obtained by the method of the present invention that consists of aforementioned step [A], step [B], and, if necessary, the stripping process.

After the purified alkyl-modified polydimethylsiloxane obtained by the method of this invention is subjected to an odor-removing treatment by the hydrogenation reaction performed in step [B], the product is free from a specific (unpleasant) odor and becomes practically odorless. Furthermore, since the product is subjected to the hydrogenation process in an organic solvent that at a temperature of 25° C. and under a pressure of 1 atmosphere has a boiling temperature equal to or greater than 70° C. and that is practically free of active hydrogen atoms, the product acquires excellent compatibility with other cosmetic raw materials, especially of a lipophilic-type, and makes it possible to form uniform mixtures. As a result, the alkyl-modified polydimethylsiloxane obtained by the method of the invention becomes suitable for use as a raw material for the preparation of various cosmetics.

If the purified product of the alkyl-modified polydimethylsiloxane obtained by the method of the present invention is emulsified, the obtained emulsion keeps good temporal stability in a wide range of temperatures (preferably in a low-temperature environment, i.e., at a temperature equal to or below 10° C.). The emulsified composition provides a clean feeling of use to a cosmetic product and, when applied, form a uniform coating film with good spreadability on skin. Since the aforementioned coating film possesses good water repellence, it imparts a long-lasting effect to cosmetic substances that contain the emulsion.

The obtained product is most suitable for use as a raw material for cosmetics among the purified products obtained by the method of the present invention is a purified alkyl-modified polydimethylsiloxane represented by above-mentioned general formula (3). The aforementioned purified alkyl-modified polydimethylsiloxane is especially suitable for use as an oil ingredient of the cosmetic raw materials, and since it possesses excellent compatibility with respect to lipophilic cosmetic raw materials (in particular to organic UV absorbers), this purified product is suitable for use as a cosmetic oil in the form of a water-in-oil emulsion-type cosmetics.

<Cosmetics>

Cosmetics of this present invention are characterized by comprising purified products of the alkyl-modified polydimethylsiloxane obtained by the method of the present invention. The cosmetics of the invention can be exemplified with those disclosed in aforementioned Patent Reference No. 3 (JP 2005-232235A) in the same manner. The combination and optional cosmetic raw materials are also disclosed in aforementioned Patent Reference No. 3.

An W/O emulsion-type cosmetic product that comprises a purified product of an alkyl-modified polydimethylsiloxane (hereinafter referred to as "water-in-oil type emulsified cosmetics") obtained by the method of the present invention may be composed of the following components:

0.1 to 95 mass % of an oil ingredient (C1) that comprises the alkyl-modified polydimethylsiloxane obtained by the method of the present invention;

0.1 to 25 mass % of a surfactant with HLB equal to or below 7 (C2); and 4.9 to 95 mass % of water.

Regarding component (C1), which is a component of the water-in-oil type emulsified cosmetic material product, is used as an indispensable component that constitutes an oil of a purified product of an alkyl-modified polydimethylsiloxane obtained by the method of the present invention, and may comprise an arbitrary component for other oils.

The aforementioned "other oils" that may be included in component (C1) for use together with the purified product of the alkyl-modified silicone are exemplified by the following: decamethyl-cyclopentasiloxane, or similar known volatile siloxanes; dimethylpolysiloxane, methylphenylpolysiloxane, 1,3,3,5-tetramethyl-1,1,5,5-tetraphenyltrisiloxane, and 1,3,5-trimethyl-1,1,3,5,5-pentaphenyltrisiloxane, or other chained siloxanes.

The "other oils" of component (C1) may be exemplified by the following: silicone oil other than cyclic silicone and chain-type silicone, a liquid isoparaffin-type hydrocarbon, an ester-type hydrocarbon, paraffin-type hydrocarbon, squalane, lanolin derivative, higher alcohol, avocado oil, palm oil, beef tallow, jojoba oil, polyalkylene glycol polyether, and its carboxylic-acid oligoester compound, terpene hydrocarbon oil, etc.

A surfactant that comprises a component (C2) of the water-in-oil type emulsion cosmetics of the invention is one that has the value of HLB (Hydrophile-Lipophile Balance) equal to or below 7. The HLB value of a surfactant is calculated with the following formula:

$$HLB = \text{"Clouding point"} A \times 0.89 + 1.11$$

If the HLB value of the surfactant exceeds 7, the hydrophilic properties of the surfactant will be extremely high. A stable water-in-oil type emulsion cosmetic will not be obtained by using such surfactant.

The surfactant that constitutes component (C2) and has a value of HLB equal to or below 7 can be represented by the following compounds: sorbitan monolaurate, sorbitan monoisostearate, sorbitan tristearate, or similar sorbitan fatty acid esters; glycerol monostearate, glycerol monooleate, or similar glycerol fatty acid esters; POE (5) hydrogenated castor oil, POE (7.5) hydrogenated castor oil, and POE (10) hydrogenated castor oil, or a similar polyoxyethylene hydrogenated castor oil, polyether-modified silicone, etc. Component (C2) is selected from the aforementioned surfactants that can be used individually or in combinations.

The surfactant that has a value of HLB equal to or below 7 and that is most suitable for use as component (C2) is a polyether-modified silicone.

The water contained in the water-in-oil type emulsion cosmetic of the invention constitutes mainly an internal phase (aqueous phase) and may comprise purified water suitable for use. Some parts of water may exist in an external phase (oil phase) in the emulsion.

The water-in-oil type emulsion cosmetic of the invention may contain an organically modified clay mineral. There are no special restrictions with regard to the organically modified clay mineral, and the one that normally is used in the preparation of cosmetic material may be added to the composition. The most preferable organically modified clay mineral is a cation-modified clay mineral treated with a water-expansive quaternary ammonium salt type surfactants.

In addition to component (C1), which is an oil ingredient, and an organically modified clay mineral (an arbitrary component), the composition may also contain other arbitrary additives, provided that these additives are not detrimental to the effects of the present invention. For example, the aforementioned additives may comprise substances normally blended with conventional cosmetics, external therapeutic preparations, etc.

They may comprise oil-soluble polymers, powders, granulated polymers, or the like. Since the purified products of the alkyl-modified silicone has excellent compatibility, in particular to lipophilic cosmetic raw materials (C3), when they form a uniform aqueous emulsion with such components, such an emulsion demonstrates stability without separation of the aforementioned products from the cosmetic material with the lapse of time.

The lipophilic cosmetic raw material (C3) possesses hydrophobic properties and at the same time has excellent compatibility or dispersibility with respect to the purified product of the alkyl-modified silicone of the present invention. This component constitutes a lipophilic cosmetic raw material which at room temperature is either absolutely insoluble in water or has a degree of solubility less than 1 wt. % per 100 g of water.

More specifically, the lipophilic cosmetic raw material that can be used as component (C3) may comprise one or more substances selected from the group consisting of a UV absorbers, silicones that are in a gum state at room temperature, silicone resins, powdered silicone elastomers, physiologically active ingredients, fragrances, and pigments. The most suitable of these for use as component (C3) are UV absorbers.

The UV absorbers may be of inorganic or organic type. If the cosmetic material of the invention is intended for use as a sunscreen cosmetic, then it is recommended that component (C3) comprises a lipophilic-type cosmetic material that contains at least one organic-type UV absorber, and more preferably, a combination of UV absorbers for protection against UV-A and UV-B radiation.

Inorganic UV absorbers can be exemplified by the following: powdered inorganic pigments, powdered metal pigments, or similar substances that may be compounded also with UV dispersants; titanium oxide, zinc oxide, cerium oxide, lower titanium oxide, iron-doped titanium oxide, or similar metal oxides; iron hydroxide, or similar metal hydroxides; plate-like metal oxide particles; aluminum flakes, or similar metal flakes; silicon carbide, or similar ceramics.

The organic UV absorbers constitute lipophilic UV protective components which can be exemplified by the following compounds: 4-(2-O-glucopyranosiloxy) propoxy-2-hydroxy benzophenone, dihydroxydimethoxy benzophenone, 2,2'-dihydroxy-4-methoxy benzophenone, 2,4-dihydroxy benzophenone, 2,2',4,4'-tetrahydroxy benophenone, 2,2'-dihydroxy-4,4'-dimethoxy benzophenone, 2-hydroxy-4-N-octoxy benzophenone, or a similar bezophenone-type compound; paramethoxy cinnamic acid 2-ethylhexyl (another name: octyl para-methoxycinnamate), glyceryl ethylhexanoate dimethoxycinnamate, methyl 2,5-diisopropyl cinnamate, 2,4,6-tris [4-(2-ethylhexyloxycarbonyl) aniline]-1,3,5-triazine, trimethoxy cinnamic acid methyl bis (trimethylsiloxy) silylisopentyl, a mixture of isopropyl paramethoxy cinnamate and diisopropyl cinnamic acid ester; diethanolamine salt of p-methoxyhydrocinnamic acid, or a similar cinnamic-acid type compound; 2-phenyl-benzoimidazole-5-sulfonic acid, 4-isopropyldibenzoyl methane, 4-tert-butyl-4'-methoxydibenzoyl methane, or a similar benzoyl-methane type compound; 2-cyano-3,3-diphenyl-propa-2-ene acid 2-ethylhexyl ester (another name: octocrylene), dimethoxybezylidene dioxoimidazolydine propionic acid 2-ethylhexyl, 1-(3,4-dimethoxyphenyl)-4,4-dimethyl-1,3-pentanediol, cinoxate, methyl-O-aminobenzoate, 2-ethylhexyl-2-cyano-3,3-diphenyl acrylate, 3-(4-benzylidene) camphor, octyl triazone, 4-3,4-dimethoxyphenylmethylene)-2,5-dioxo-1-imidazolydine propionic acid 2-ethylhexyl, as well as high-polymer and silane derivatives of the above-mentioned compounds.

The physiologically active ingredient is a lipophilic substance that, when applied onto the skin, exerts a physiological effect. Examples include anti-inflammatory agents, age resisters, pore-tightening preparations, hair-growing agents, hair tonics, moisture-retaining agents, blood-circulation promoting agents, drying agents, cold-sense agents, warm-sense agents, vitamins, amino acids, wound healing promoters, irritation emollients, analgesic preparations, cell activating agents, etc. Among these, most preferable for use are natural lipophilic substances such as plant extracts, seaweed extracts, and herbal ingredients.

There are no special restrictions with regard to the lipophilic fragrances that can be used for the purposes of the invention, and such substances may comprise extracts from plants, seeds, leaves and roots of various plants, fragrances extracted from seaweeds, fragrances or secretion products extracted from various parts of the animal body (e.g., musks or sperm), artificially synthesized fragrances (such as menthol, mask, ester acetate, vanilla). The fragrance can be added to cosmetics for imparting to them scent and aroma. Coloring substances may comprise oil-soluble dyes, organic pigments, and lipophilic fluorescent brighteners.

Besides water, the aqueous phase of the cosmetic material of the invention may be combined with some arbitrary additives. Such components of the aqueous phase may comprise, e.g., a vitamin B group, vitamin C, their derivatives, pantothenic acid and its derivatives, biotin, and similar vitamins, or other water-soluble substances; sodium glutamate, arginine, aspartic acid, citric acid, tartaric acid, lactic acid, or similar buffering agents; EDTA, or similar chelating agents; water-soluble ultraviolet absorbers, various coloring agents, etc. These substances can be used without special restrictions. To improve the storage stability of the cosmetic material, the latter may also be combined with pH adjusters, antiseptic agents, antibacterial agents, antioxidants, etc.

The internal phase (aqueous phase) of the water-in-oil type emulsion cosmetic of the invention also may be comprised of an oil-in-water (O/W) type of emulsion prepared by dispersing microscopic particles of the oil ingredient. The emulsified composition (O/W/O emulsion) having the above-described emulsion as an internal phase (dispersed particles) also is covered by the scope of the present invention.

Unless the effect of the present invention is impaired, the water-in-oil type of emulsion cosmetic of the present invention may be blended with a polyhydric alcohol, its derivative, and a moisturizing agent that improves the moisture-retaining effect. Various water-soluble polymers can also be added. Such polymers can be represented by natural, semi-synthetic, or synthetic water-soluble polymers, as well as by inorganic water-soluble polymers.

The water-in-oil type emulsion cosmetics of this invention may be used as skin cosmetics, hair cosmetics, or the like.

The water-in-oil type emulsion cosmetic of this invention can be manufactured according to conventional methods. According to one example of the manufacturing method, an oil ingredient that contains a purified product of alkyl-modified silicone is uniformly mixed with a surfactant and then the obtained premixed composition, when stirred, is combined with gradually added water. The obtained mixture is uniformly stirred.

EXAMPLES

The invention will now be described in more detail with reference to the Practical Examples, which, however, should not be construed as limiting the scope of the invention application.

[Odor Test]
A 200 ml capacity of cover-equipped glass bottle was filled with the sample material to about 80% of its volume, kept for more than 1 hour at 25° C. in a thermostat, and then the odor in the interior of the bottle was evaluated according to the criteria given as below. The results are shown in Table 1.
 ⊚: odor is practically undetectable
 O: slight (ether-like) odor is felt
 Δ: some (ether-like) odor is felt
 X: (ether-like) odor is distinctly felt

[Compatibility with Cosmetic Material Components]
The alkyl-modified trisiloxane and the ethylhexyl methoxycinnamate (organic UV absorber; the product of BASF Company, trademark: UVINUL®MC80N) used in subsequent Application and Comparative Examples were mixed in a glass vial in a 1:1 weight ratio and left intact.
Five minutes later, the compatibility of each samples are evaluated on the basis of criteria given as below. The results are presented in Table 1 given below.
 O: solution is transparent
 Δ: microscopic turbidity is observed
 X: white turbidity of the solution Practical Example 1

(1) Step [A]:
A glass-made reactor equipped with a stirrer, a reflux condenser, thermometer, and a nitrogen supply inlet port was loaded with 1000 parts by mass of 1,1,13,5,5,5-heptamethyltrisiloxane and 0.100 parts by mass of a 10% ethanol solution of a chloroplatinic acid (catalyst). When stirred, the components were heated and after the temperature of the solution was stabilized at 74° C., a supply of 1-octene by dripping was initiated. A hydrosilation reaction that occurred in that case was accompanied by generation of exothermic heat. The total amount of the added 1-octane (555 parts by mass) was gradually added in drops so that the temperature of the solution did not exceed 120° C. After completion of dripping of 1-octene, stirring was continued. One hour later, the solution was sampled. Since mixing of the product with a water/ethanol solution of a potassium hydroxide did not generate any hydrogen gas, it could be concluded that the hydrosilation reaction was completed. Following this, the reaction solution (at 85° C.) was combined with 1.55 parts by mass of sodium hydrogen carbonate, and the mixture was neutralized by stirring and mixing for 30 min.
Next, the pressure in the reactor was reduced under nitrogen supply conditions, the product was heated to 120° C., and low-boiling-point components (light-mass substances) were removed (Stripping Step) for 1 hour at a pressure of 1.3 kPa. The obtained reaction product was cooled to room temperature, normal pressure was restored, the product was mixed with diatomaceous earth, and solid/liquid phases were separated (removal of the catalyst) by subjecting the product to pressure filtration. The obtained filtrate comprised 1300 parts by mass of a crude alkyl-modified polydimethylsiloxane represented by chemical formula (1) given below:

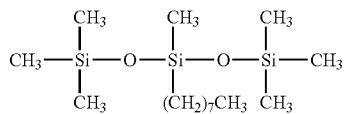

Formula [i]

The obtained crude product had an appearance of a uniform, slightly yellow, transparent liquid. The crude product had an unpleasant odor immediately after the preparation.

(2) Step [B]:
A stainless-steel autoclave equipped with a stirrer and having a 1 liter of capacity was loaded with a mixture of 400 parts by mass of the aforementioned crude alkyl-modified polydimethylsiloxane and 16 parts by mass of a Raney nickel catalyst (hydrogenation catalyst; the Raney nickel catalyst was used after solvent-replacements with methylcyclohexane in five times preliminarily). Following this, 10 parts by mass of methylcyclohexane were added as a solvent. The gaseous phase of the autoclave was replaced with hydrogen, and the hydrogen pressure was increased to 8.0 MPa. When the system was stirred, the temperature was gradually increased, and a deodorization treatment was carried out by conducting the hydrogenation reaction for 6 hours at 140° C.

(3) Post-Treatment Step (Catalyst Separation and Stripping Step):
The reaction product obtained in Step [B] was cooled to 40° C., hydrogen was blown out and replaced with nitrogen.
Next, the Raney catalyst was removed from the reaction product by pressure filtration. The obtained filtrate was loaded into a two-neck flask having 1 liter capacity and provided with a reflux cooler and a nitrogen-supply port. With supplying nitrogen into the flask, the pressure in the flask was reduced and the temperature was increased to 120° C. Under the pressure of 1.3 kPa, low-boiling-point components (light-mass substances) were removed for 5 hours. The condensate of the liquid filtrate was obtained as 370 parts by mass of a purified product of an alkyl-modified dimethylpolysiloxane (P1) of aforementioned formula (i).

Practical Example 2

A purified product of an alkyl-modified dimethylpolysiloxane (P2) of aforementioned formula (i) was obtained in the same manner as in Step [B] of Practical Example 1, except that an equivalent amount of ethylcyclohexane was used instead of the methylcyclohexane.

Comparative Example 1

A purified product of an alkyl-modified dimethylpolysiloxane (C1) of aforementioned formula (i) was obtained in the same manner as in Step [B] of Practical Example 1, except that an equivalent amount of isopropanol was used instead of the methylcyclohexane.

Comparative Example 2

A purified product of an alkyl-modified dimethylpolysiloxane (C2) of aforementioned formula (i) was obtained in the same manner as in Step [B] of Practical Example 1, except that an equivalent amount of n-butanol was used instead of the methylcyclohexane.

Comparative Example 3

A purified product of an alkyl-modified dimethylpolysiloxane (C3) of aforementioned formula (i) was obtained in the same manner as in Step [B] of Practical Example 1, except that an equivalent amount of tetrahydrofurane (THF, boiling point: 66° C.) was used instead of the methylcyclohexane.
The purified products of the alkyl-modified dimethylpolysiloxane obtained in Practical Examples 1 to 2 and in Comparative Examples 1 to 3 were evaluated with regard to odor and compatibility with lipophilic cosmetic raw materials. The results are shown in Table 1. None of the purified products of alkyl-modified dimethylpolysiloxane obtained in practical examples of the invention produced an unpleasant odor, and all purified products of this invention were practically odorless. The products of this invention showed uniform compatibility with methoxy cinnamic acid ethylhexyl(an organic UV absorber). On the other hand, just after its production, the purified products of the alkyl-modified dimethylpolysiloxane obtained in Comparative Examples had an odor and could not provide uniform mixture with methoxy cinnamic acid ethylhexyl(an organic UV absorber).

TABLE 1

|  | Pr. Ex. 1 | Pr. Ex. 2 | Comp. Ex. 1 | Comp. Ex. 2 | Comp. Ex. 3 |
|---|---|---|---|---|---|
| Replacement solvent | Methyl cyclo-hexane | Ethyl cyclo-hexane | Isopropanol | n-butanol | Tetrahydrofurane (THF) |
| Odor test | ◎ | ◎ | Δ | Δ | ○ |
| Compatibility with cosmetic product components | ○ | ○ | X | X | Δ |

The invention claimed is:

1. A method of manufacturing a purified product of an alkyl-modified polydimethylsiloxane having the following general formula (1):

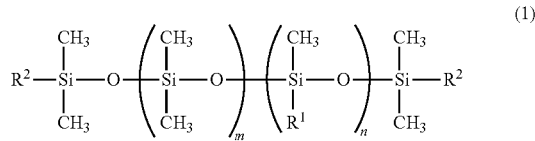

where $R^1$ is an alkyl group of formula $—C_2H_4—C_pH_{2p+1}$ that contains 2 to 30 carbon atoms, where "p" is a number ranging from 0 to 28, $R^2$ is a methyl group or a group defined earlier for $R^1$; "m" is a number ranging from 0 to 300; and "n" is a number ranging from 0 to 50; however, when "n" is 0, at least one $R^2$ is a group indicated by $R^1$, the method comprising the steps of:

[A] synthesizing an alkyl-modified polydimethylsiloxane of general formula (1) by subjecting
a hydrosilyl-containing polydimethylsiloxane (a) having the following formula (2):

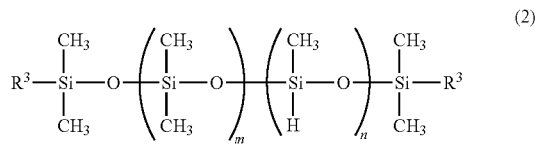

where $R^3$ is a methyl group or a hydrogen atom; and "m" and "n" are each individually numbers in the same ranges as defined above; however, when "n" is 0, at least one $R^3$ is a hydrogen atom, and
an α-olefin of general formula $CH_2=CH—C_pH_{2p+1}$ (b) that contains 2 to 30 carbon atoms where "p" is a number ranging from 0 to 28, to a hydrosilation reaction, and

[B] subjecting the crude alkyl-modified polydimethylsiloxane obtained in Step [A] to a treatment of rendering it odorless by a hydrogenation reaction that is carried out at a temperature of 25° C. in the presence of a hydrogenation catalyst in methylcyclohexane and/or ethylcyclohexane, wherein the methylcyclohexane and/or ethylcyclohexane have a boiling point equal to or greater than 70° C. under a pressure of 1 atmosphere.

2. The method of manufacturing a purified product of an alkyl-modified polydimethylsiloxane according to claim 1, wherein the hydrogenation catalyst used in Step [B] is a Raney nickel.

3. The method of manufacturing a purified product of an alkyl-modified polydimethylsiloxane according to claim 1, wherein step [A] comprises a step [A1] of synthesizing an alkyl-modified polydimethylsiloxane of formula (3) given below:

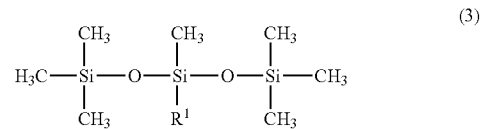

where $R^1$ is the same as defined earlier,
by subjecting 1,1,1,3,5,5,5-heptamethyltrisiloxane (a1) and an α-olefin of general formula $CH_2=CH—C_pH_{2p+1}$ that contains 2 to 30 carbon atoms where "p" is a number ranging from 0 to 28, to a hydrosilation reaction, and wherein step [B] comprises a step [B1] of subjecting the crude alkyl-modified polydimethylsiloxane obtained in Step [A1] in the presence of a hydrogenation catalyst to a treatment of rendering it odorless by a hydrogenation reaction in methylcyclohexane or ethylcyclohexane.

4. The method of manufacturing a purified product of an alkyl-modified polydimethylsiloxane according to claim 1, comprising a step of stripping of light fractions by distillation from the crude alkyl-modified polydimethylsiloxane or a product of hydrogenation thereof, prior to or after Step [B], wherein the stripping is carried out by bringing the crude alkyl-modified polydimethylsiloxane or a product of hydrogenation thereof into contact with gaseous nitrogen under a reduced pressure.

5. The method of manufacturing a purified product of an alkyl-modified polydimethylsiloxane according to claim 2, wherein step [A] comprises a step [A1] of synthesizing an alkyl-modified polydimethylsiloxane of formula (3) given below:

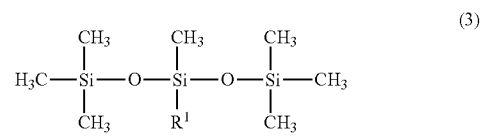

where $R^1$ is the same as defined earlier,
by subjecting 1,1,1,3,5,5,5-heptamethyltrisiloxane (a1) and an α-olefin of general formula $CH_2=CH—C_pH_{2p+1}$ that contains 2 to 30 carbon atoms where "p" is a number ranging from 0 to 28, to a hydrosilation reaction, and wherein step [B] comprises a step [B1] of subjecting the crude alkyl-modified polydimethylsiloxane obtained in Step [A1] in the presence of a hydrogenation catalyst to a treatment of rendering it odorless by a hydrogenation reaction in methylcyclohexane and/or ethylcyclohexane.

6. The method of manufacturing a purified product of an alkyl-modified polydimethylsiloxane according to claim 2, comprising a step of stripping of light fractions by distillation from the crude alkyl-modified polydimethylsiloxane or a product of hydrogenation thereof, prior to or after Step [B], wherein the stripping is carried out by bringing the crude alkyl-modified polydimethylsiloxane or a product of hydrogenation thereof into contact with gaseous nitrogen under a reduced pressure.

7. The method of manufacturing a purified product of an alkyl-modified polydimethylsiloxane according to claim 3, comprising a step of stripping of light fractions by distillation from the crude alkyl-modified polydimethylsiloxane or a product of hydrogenation thereof, prior to or after Step [B], wherein the stripping is carried out by bringing the crude alkyl-modified polydimethylsiloxane or a product of hydrogenation thereof into contact with gaseous nitrogen under a reduced pressure.

8. The method of manufacturing a purified product of an alkyl-modified polydimethylsiloxane according to claim 5, comprising a step of stripping of light fractions by distillation from the crude alkyl-modified polydimethylsiloxane or a product of hydrogenation thereof, prior to or after Step [B], wherein the stripping is carried out by bringing the crude alkyl-modified polydimethylsiloxane or a product of hydrogenation thereof into contact with gaseous nitrogen under a reduced pressure.

9. A method of manufacturing a purified product of an alkyl-modified polydimethylsiloxane having the following general formula (1):

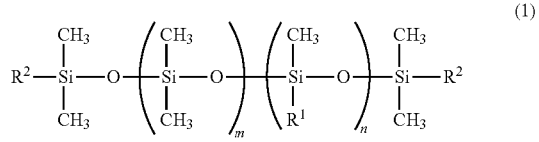

where $R^1$ is an alkyl group of formula —$C_2H_4$—$C_pH_{2p+1}$ that contains 2 to 30 carbon atoms, where "p" is a number ranging from 0 to 28, $R^2$ is a methyl group or a group defined earlier for $R^1$; "m" is a number ranging from 0 to 300; and "n" is a number ranging from 0 to 50; however, when "n" is 0, at least one $R^2$ is a group indicated by $R^1$, the method comprising the steps of:

[A] synthesizing an alkyl-modified polydimethylsiloxane of general formula (1) by subjecting:

a hydrosilyl-containing polydimethylsiloxane (a) having the following formula (2):

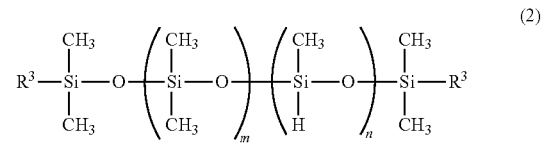

where $R^3$ is a methyl group or a hydrogen atom; and "m" and "n" are each individually numbers in the same ranges as defined above; however, when "n" is 0, at least one $R^3$ is a hydrogen atom, and an α-olefin of general formula $CH_2$=$CH$—$C_pH_{2p+1}$ (b) that contains 2 to 30 carbon atoms where "p" is a number ranging from 0 to 28, to a hydrosilation reaction;

[B] subjecting the crude alkyl-modified polydimethylsiloxane obtained in Step [A] to a treatment of rendering it odorless by a hydrogenation reaction that is carried out at a temperature of 25° C. in the presence of a hydrogenation catalyst in methylcyclohexane and/or ethylcyclohexane;

[C] stripping of light fractions by distillation from the crude alkyl-modified polydimethylsiloxane or a product of hydrogenation thereof, prior to or after Step [B], wherein the stripping is carried out by bringing the crude alkyl-modified polydimethylsiloxane or a product of hydrogenation thereof into contact with gaseous nitrogen under a reduced pressure; and

[D] mixing the stripped crude alkyl-modified polydimethylsiloxane or a product of hydrogenation thereof of step [C] with a lipophilic material which has a degree of solubility of less than 1 wt. % per 100 g of water at room temperature.

10. The method of manufacturing a purified product of an alkyl-modified polydimethylsiloxane according to claim 9, wherein said lipophilic material is selected from the group consisting of UV absorbers, silicones that are in a gum state at room temperature, silicone resins, powdered silicone elastomers, physiologically active ingredients, fragrances, and pigments.

11. The method of manufacturing a purified product of an alkyl-modified polydimethylsiloxane according to claim 9, wherein said lipophilic material is an organic UV absorber.

12. The method of manufacturing a purified product of an alkyl-modified polydimethylsiloxane according to claim 11, wherein said lipophilic material comprises ethylhexyl methoxycinnamate.

* * * * *